United States Patent
Ok et al.

(10) Patent No.: US 7,274,455 B2
(45) Date of Patent: Sep. 25, 2007

(54) OPTICAL DETECTION APPARATUS FOR MULTI-CHANNEL MULTI-COLOR MEASUREMENT AND MULTI-CHANNEL SAMPLE ANALYZER EMPLOYING THE SAME

(75) Inventors: Gyeong-sik Ok, Busan (KR); Jin-tae Kim, Gyeonggi-do (KR); Kwang-wook Oh, Gyeonggi-do (KR); Sang-hyo Kim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 197 days.

(21) Appl. No.: 11/221,055

(22) Filed: Sep. 7, 2005

(65) Prior Publication Data

US 2006/0050277 A1   Mar. 9, 2006

(51) Int. Cl.
*G01N 21/25* (2006.01)
*G01J 3/51* (2006.01)

(52) U.S. Cl. ............... 356/417; 356/418; 356/419; 250/226

(58) Field of Classification Search .......... 356/417, 356/418, 419; 250/226; 385/18
See application file for complete search history.

(56) References Cited

U.S. PATENT DOCUMENTS

| | | | | |
|---|---|---|---|---|
| 3,697,185 A | * | 10/1972 | Kassel et al. | 356/410 |
| 4,084,909 A | * | 4/1978 | Mathisen | 356/332 |
| 4,446,366 A | * | 5/1984 | Brogardh et al. | 250/227.23 |
| 4,477,190 A | * | 10/1984 | Liston et al. | 356/418 |
| 5,633,751 A | * | 5/1997 | Tanaami et al. | 359/368 |
| 5,940,183 A | | 8/1999 | Miller | |
| 6,429,936 B1 | | 8/2002 | Scaduto | |
| 6,856,720 B2 | * | 2/2005 | Baugh | 385/22 |
| 2005/0046981 A1 | * | 3/2005 | Karube et al. | 359/891 |
| 2006/0072873 A1 | * | 4/2006 | Tekippe et al. | 385/18 |
| 2006/0202133 A1 | * | 9/2006 | Ok et al. | 250/458.1 |
| 2007/0081252 A1 | * | 4/2007 | Lin et al. | 359/618 |

FOREIGN PATENT DOCUMENTS

| WO | WO8300384 | 2/1983 |
|---|---|---|
| WO | WO2004059269 | 7/2004 |

OTHER PUBLICATIONS

European Search Report; EP05019263; Mar. 20, Apr. 4, 2007 All the references cited in the Search Report are listed above.

* cited by examiner

*Primary Examiner*—Gregory J. Toatley, Jr.
*Assistant Examiner*—Bryan J Giglio
(74) *Attorney, Agent, or Firm*—Cantor Colburn LLP

(57) ABSTRACT

Provided are an optical detection apparatus which can measure multi-channel samples at high speed and various wavelengths using an optical detector and a multi-channel sample analyzer employing the same. The optical detection apparatus includes an optical detector; a filter wheel having at least two color filters connected to each other in the shape of a disk; a plurality of optical channels through which a plurality of beams of light enter the filter wheel; and a mirror unit including a plurality of mirrors for sequentially reflecting the plurality of beams of light transmitted through the filter wheel to the optical detector, wherein the mirror unit rotates together with the filter wheel.

19 Claims, 5 Drawing Sheets

OPTICAL DETECTION APPARATUS FOR MULTI-CHANNEL MULTI-COLOR MEASUREMENT AND MULTI-CHANNEL SAMPLE ANALYZER EMPLOYING THE SAME

BACKGROUND OF THE INVENTION

This application claims the benefit of Korean Patent Application No. 10-2004-0071224, filed on Sep. 7, 2004, in the Korean Intellectual Property Office, the disclosure of which is incorporated herein in its entirety by reference.

1. Field of the Invention

The present invention relates to an optical detection apparatus for multi-channel multi-color measurement and a multi-channel sample analyzer employing the same, and more particularly, to an optical detection apparatus which can measure multi-channel samples at high speed and various wavelengths using an optical detector and a multi-channel sample analyzer employing the same.

2. Description of the Related Art

A method of analyzing components of a sample which includes irradiating a specific wavelength of light onto the sample and then detecting a spectrum of light which is emitted from the sample is well known. For example, the respective bases of DNA can be labeled with fluorescent dyes having different emission wavelengths, and then the intensity light emitted from the fluorescent dyes is analyzed, thereby identifying the base sequence of the DNA.

FIG. 1 is a schematic diagram of a conventional fluorescent analyzer 100. Referring to FIG. 1, the conventional fluorescent analyzer 100 includes an optical unit 110 for irradiating light onto a sample 130 and a detection unit 120 for detecting light emitted from the sample 130. The optical unit 110 generally includes a light source 112, a dichroic mirror 114, an objective lens 115, and a sample holder 117. The detection unit 120 includes an optical detector 125, for example, a photo mutiplier tube (PMT), and a filter 121 which transmits a specific wavelength of light, etc. The light source 112 may include various sources, such as a halogen lamp, a light-emitting diode (LED), a laser, etc. Light emitted from the light source 112 is reflected by the dichroic mirror 114 and is partially absorbed by the sample 130 on the sample holder 117. The light emitted from the sample 130 is transmitted through the dichroic mirror 114 and enters the detection unit 120. The light which enters the detection unit 120 is transmitted through the filter 121, thus having a specific wavelength and the optical detector 125 detects the intensity of light having the specific wavelength. By analyzing the intensity of the fluorescence light emitted from the sample by varying the wavelength property of the filter 121 or the light source 110, the analyte of the sample can be identified.

Recently, to increase the efficiency of analyzing a sample and determine the identity of the sample at high speed, a multi-channel sample analyzer, which can analyze a plurality of samples at once, has been developed. Multi-channel sample analysers can be roughly classified into apparatuses which determine a plurality of samples simultaneously using a plurality of optical detectors and apparatuses which determine a plurality of samples sequentially using an optical detector.

Examples of the apparatuses which determine a plurality of samples simultaneously using a plurality of optical detectors include one which uses a number of separate optical detectors equal to the number of the samples, and the optical detectors detect the light emitted from the respective samples (for example, Cepheid Smart Cycler[R]) and one in which a large area of light is irradiated to a plurality of samples at a time and a CCD having a large area detects the lights emitted from the samples (for example, ABI Prism 7000[R] and BioRad iCycler[R]). However, when the number of separate optical detectors is equal to the number of the samples, filters which can cover a band of wavelength to be examined are disposed in front of the respective optical detectors. Thus, too many optical detectors and filters are used relative to the number of samples. On the other hand, when the CCD is used, only one filter wheel may be used. However, a CCD having a large area and a high accuracy required for fluorescent analysis is very expensive, thus increasing the production costs of the multi-channel sample analyzer and being unsuitable for small analyzers. Referring to FIG. 2, a rotating filter wheel is generally disposed in front of the CCD to perform multi-channel analysis using a variety of wavelengths. However, since a frame rate (the number of images which a CCD reads per second), which is related to a resolution of the CCD measurement, is limited, an increase in speed of the filter wheel is limited. Thus, there is still a limit when measuring many wavelengths at high speed.

In an apparatus for determining a plurality of samples sequentially using an optical detector, generally, a plurality of samples are placed on a sample holder and the samples are measured by scanning. As described above, to perform the spectroscopic analysis of a sample at many wavelengths, the filter wheel should be rotated. Thus, a total measuring time calculated by multiplying a scanning time of the sample by a rotation time of the filter wheel can be increased.

Thus, there is a need for a detection unit which can detect a plurality of samples at high speed and various wavelengths using an optical detector and a filter wheel.

SUMMARY OF THE INVENTION

The present invention provides an optical detection apparatus which can measure multi-channel samples at high speed and various wavelengths using an optical detector and a multi-channel sample analyzer employing the same.

The present invention also provides an optical detection apparatus for multi-channel multi-color measurement, which can have a small size and low production costs, and a multi-channel sample analyzer employing the same.

According to an aspect of the present invention, there is provided an optical detection apparatus for multi-channel multi-color measurement comprising: an optical detector; a filter wheel having at least two color filters connected to each other in the shape of a disk; a plurality of optical channels through which a plurality of beams of light enter the filter wheel; and a mirror unit including a plurality of mirrors for sequentially reflecting the plurality of beams of light transmitted through the filter wheel to the optical detector, wherein the mirror unit rotates together with the filter wheel.

The optical channels may be arranged in a row above the filter wheel along the radius direction of the filter wheel on a line connecting the center of the filter wheel to the optical detector. The optical channels farther from the optical detector may be shorter than the optical channels closer to the optical detector.

Each of the mirrors of the mirror unit may correspond to one of the optical channels such that the beams of light exiting the optical channels are reflected to the optical detector and the mirrors may be disposed at the same radial positions as the corresponding optical channels. The mirrors in the mirror unit may be disposed at different azimuthal angles from one another on the mirror unit such that the beams of light exiting the optical channels are sequentially reflected to the optical detector during the rotation of the mirror unit.

According to another aspect of the present invention, there is provided a multi-channel sample analyzer comprising: a light source unit for irradiating light onto each of a plurality of samples; an optical detection unit for detecting light beams emitted from the plurality of samples; and an optical transport unit for receiving the light beams emitted from the plurality of samples and transporting them to the optical detection unit, wherein the optical detection unit comprises an optical detector; a filter wheel having at least two color filters connected to each other in the shape of a disk; a plurality of optical channels through which a plurality of beams of light transported from the optical transport unit enter the filter wheel; and a mirror unit including a plurality of mirrors for sequentially reflecting each of the plurality of beams of light transmitted through the filter wheel to the optical detector, wherein the mirror unit rotates together with the filter wheel.

The optical transport unit may comprise a light receiver for receiving the beams of light emitted from the samples and an optical fiber for transporting the beams of light from the light receiver to the optical detection unit.

The multi-channel sample analyzer may further comprise a dichroic mirror for letting the light emitted from the light source unit proceed to the samples and letting the beams of light emitted from the samples proceed to the optical transport unit; a sample holder for holding the samples; and a driving unit for rotating the filter wheel and the mirror unit.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the constitution and operation of an optical detection apparatus for multi-channel multi-color measurement according to an embodiment of the present invention and a multi-channel sample analyzer employing the same will be described in more detail with reference to the attached drawings.

Figure 1:
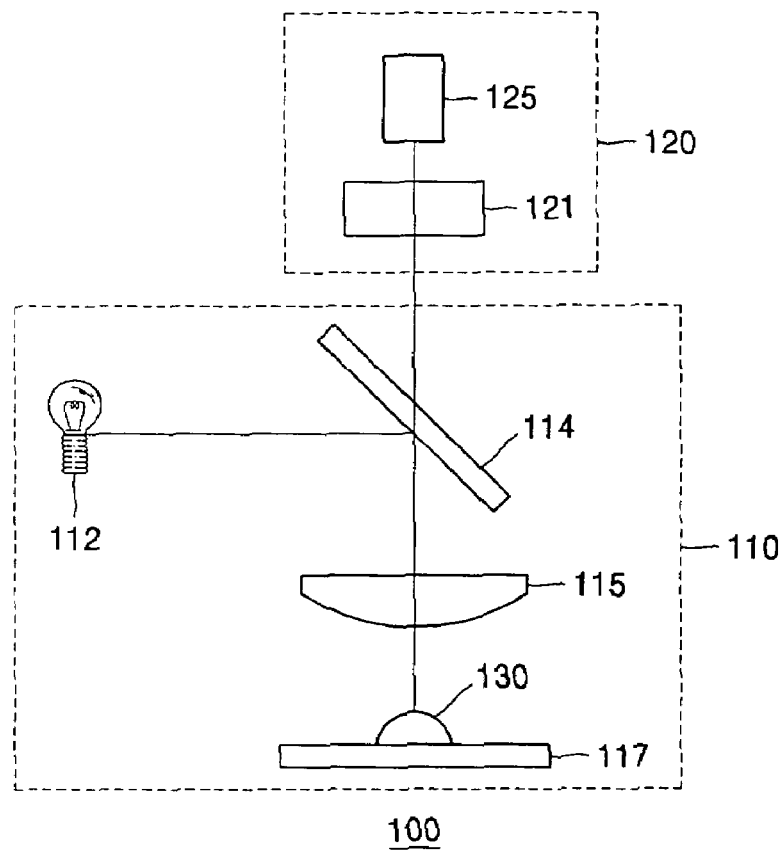
FIG. 1 is a schematic diagram of a conventional apparatus for fluorescence analysis.
Figure 2:
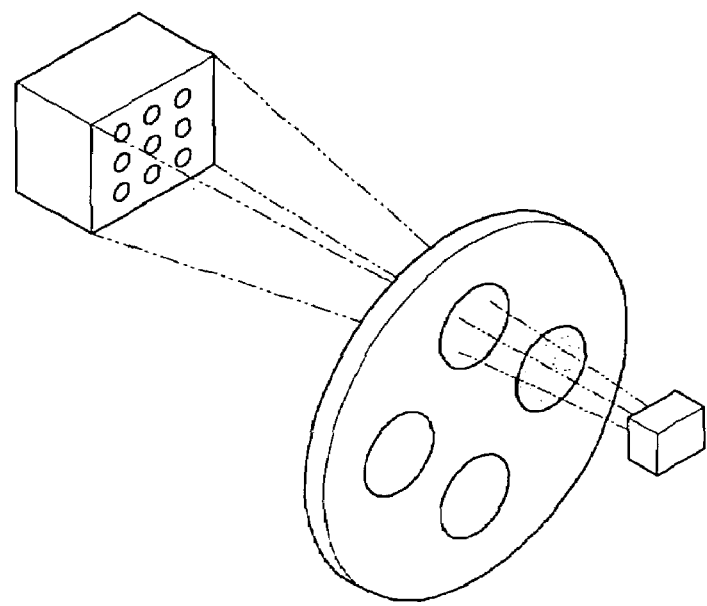
FIG. 2 is a schematic diagram of a conventional optical detection apparatus for multi-color measurement using a filter wheel.
Figure 3:
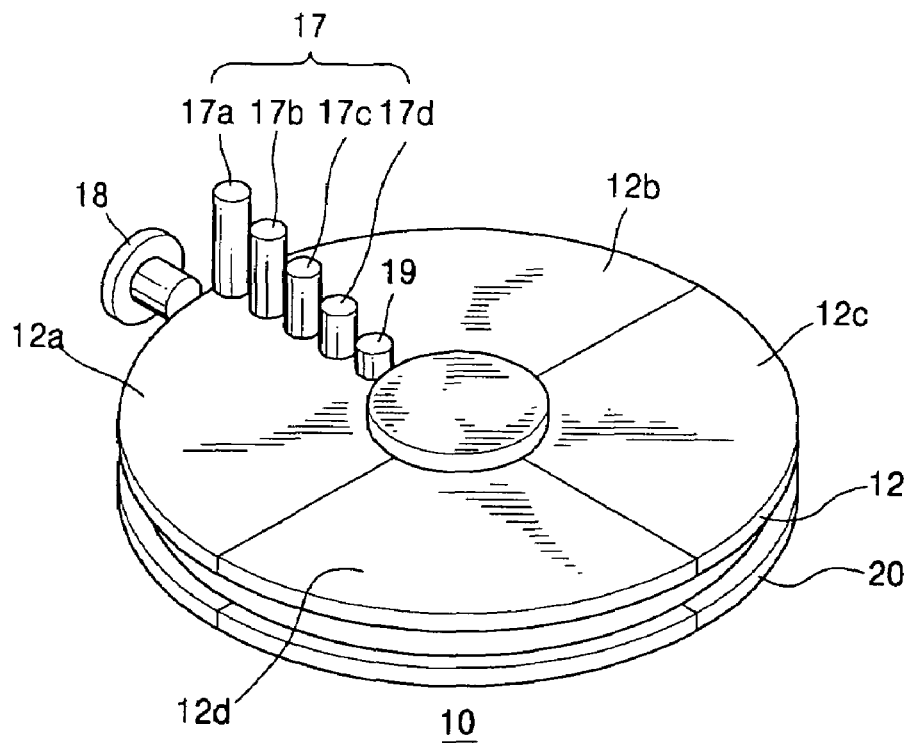
FIG. 3 is a schematic perspective view of an optical detection apparatus according to an embodiment of the present invention.

FIG. 3 is a schematic perspective view of an optical detection apparatus 10 according to an embodiment of the present invention. Referring to FIG. 3, the optical detection apparatus 10 comprises an optical detector 18, for example, a photo multiplier tube (PMT), a filter wheel 12 having first through fourth color filters 12a through 12d connected to each other to form a disk form, a plurality of optical channels 17 and 19 through which a plurality of wavelengths of light enter the filter wheel 12, and a mirror unit 20 having a plurality of mirrors 21 through 25 that sequentially reflect the wavelengths of light transmitted through the filter wheel 12 to the optical detector 18. The optical detection apparatus 10 may further comprise, for example, a spindle motor 15 for rotating the filter wheel 12 and the mirror unit 20 at the same speed. The optical channels 17a through 17d let the light emitted from samples enter the filter wheel 12 and the optical channel 19 lets mark light for indicating one cycle of rotation of the filter wheel 12 enter the filter wheel 12. Thus, the optical channel 19 may be a laser diode, for example. As illustrated in FIG. 3, the optical channels 17 and 19 are arranged in a row above the filter wheel 12 along a radial direction of the filter wheel 12 on a line connecting a rotational center of the filter wheel 12 to the optical detector 18. Although FIG. 3 illustrates the filter wheel 12 composed of the first through fourth color filters 12a through 12d, this is shown for the purpose of illustration and the number of the color filters is not limited to four.

Figure 4:
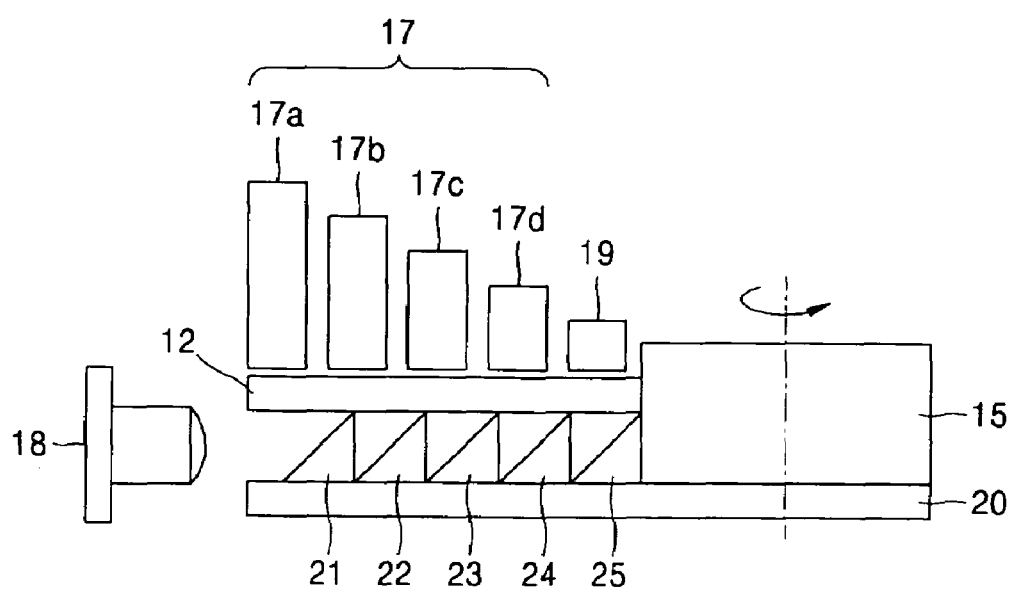
FIG. 4 is a schematic cross-sectional view of the optical detection apparatus illustrated in FIG. 3.

FIG. 4 is a schematic cross-sectional view of the optical detection apparatus 10 illustrated in FIG. 3. Referring to FIG. 4, the optical detector 18 is near the circumference of the filter wheel 12 and the mirror unit 20. The optical detector 18 detects the light reflected by the mirror unit 20. In the mirror unit 20, the plurality of mirrors 21 through 25 face the plurality of optical channels 17a, 17b, 17c, 17d and 19, respectively, and reflect the light to the optical detector 18.

Figure 5:
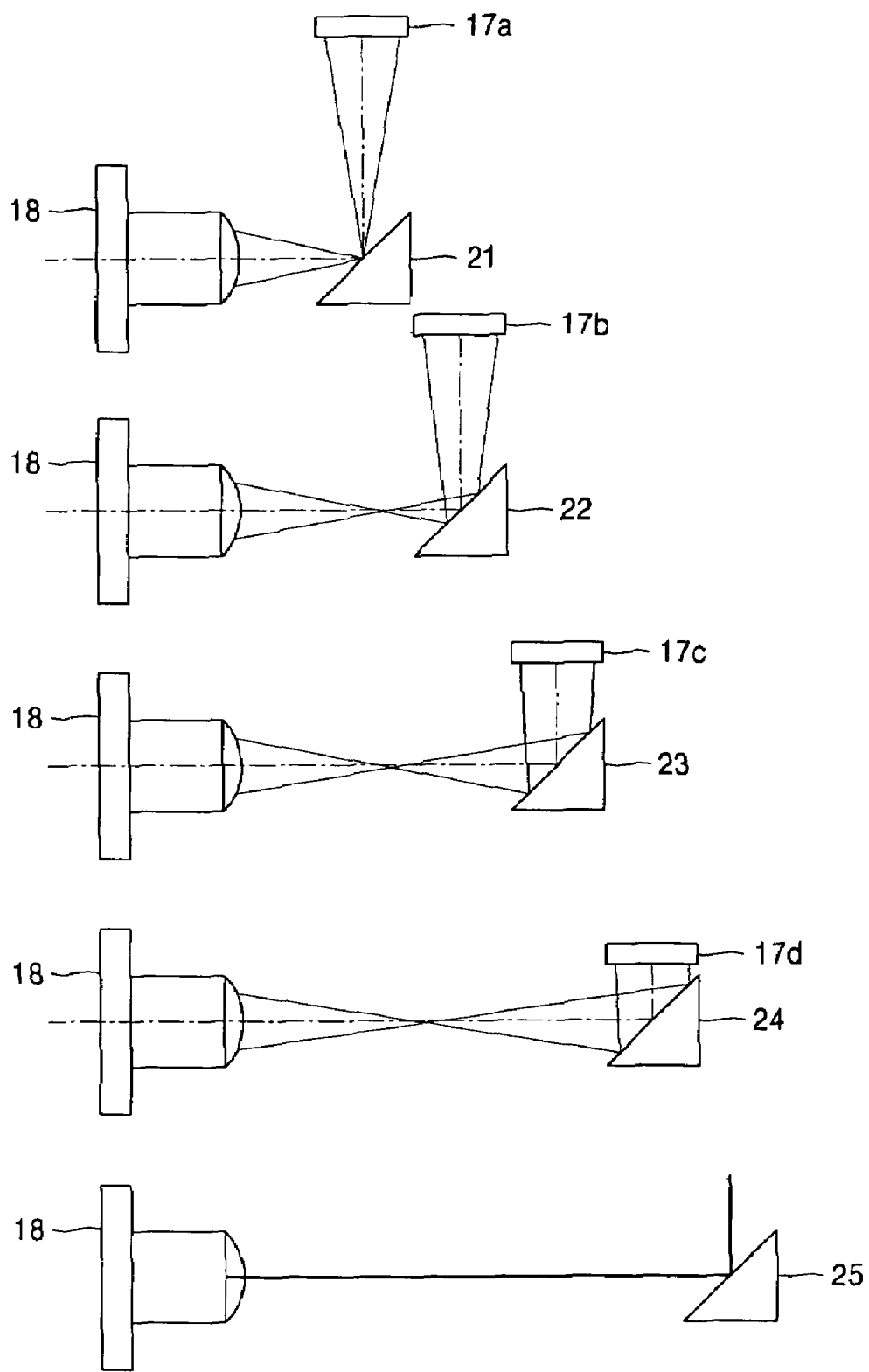
FIG. 5 is a schematic diagram illustrating a principle of the optical detection apparatus according to an embodiment of the present invention.

To ensure that the optical paths of the light exiting the plurality of optical channels 17 and 19 all have the same length, the lengths of the optical channels 17 and 19 become shorter for the optical channels 17 and 19 closer to the center of the filter wheel 12. This is illustrated in FIG. 5. Referring to FIG. 5, to ensure that the optical detector 18 may accurately measure the strength of incident light, it is advantageous that the light enters uniformly through the detection surface of the optical detector 18. To this end, the beams of light which enter the optical channels 17 and 19 must all be focused. In addition, to ensure that the beams of light which exit the optical channels 17 and 19 are all focused onto the detection surface of the optical detector 18 in the same manner, the lengths of the respective optical paths between the optical detector 18 and the optical channels 17 and 19 must be equal. Thus, the optical channel 17a facing the mirror 21 which is closest to the optical detector 18 is longest among the optical channels 17 and 19. That is, the optical path between the optical channel 17a and the mirror 21 is longest. In this way, as illustrated in FIG. 5, the further the mirror is away from the optical detector 18, the shorter the length of the corresponding optical channel. Lenses for focusing the light may be installed in respective incident portions of the optical channels 17.

Figure 6:
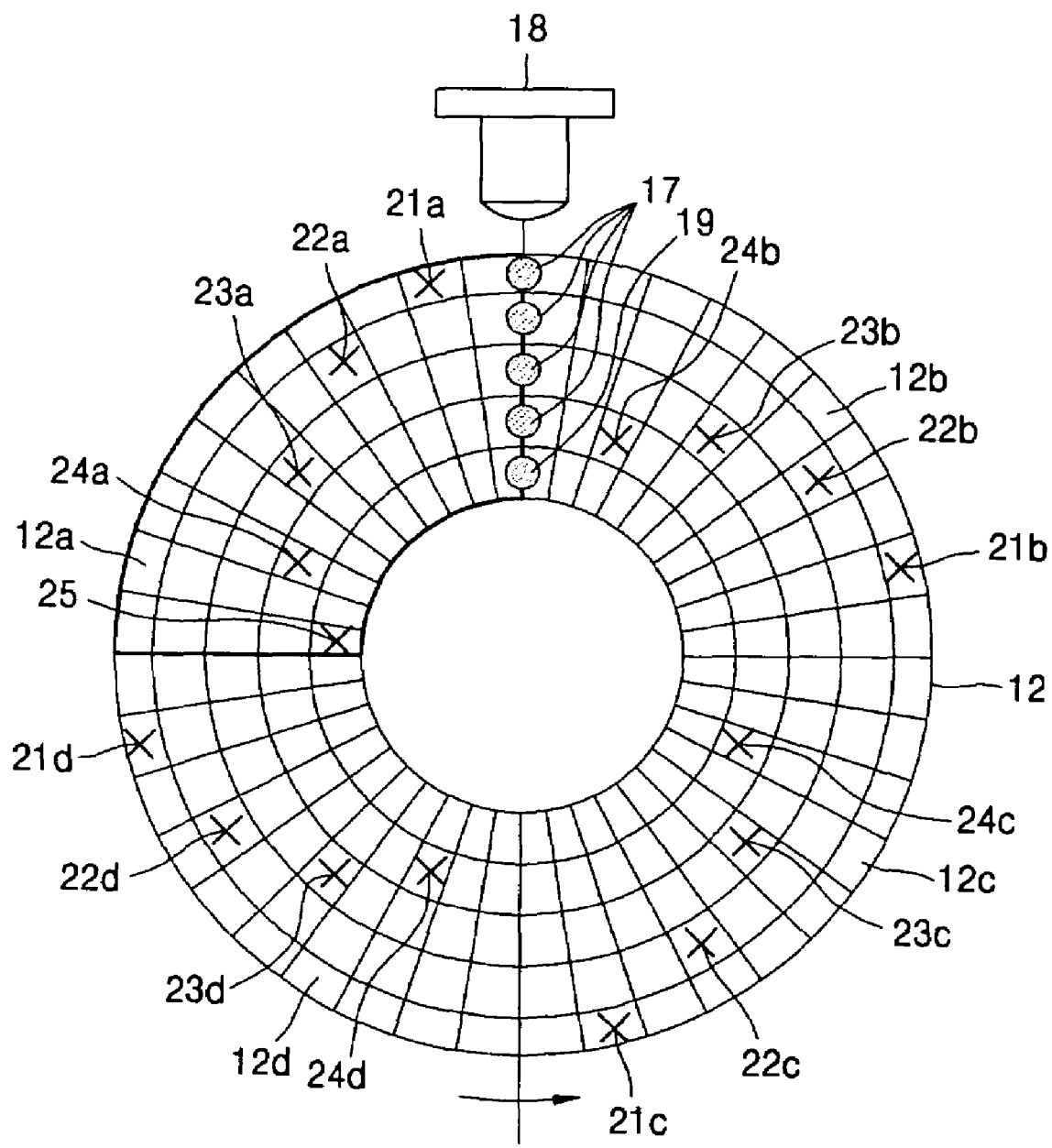
FIG. 6 is a schematic top plan view of the optical detection apparatus illustrated in FIG. 3.

If the plurality of mirrors 21 through 25 in the mirror unit 20 are arranged in a row along a radial direction of the filter wheel 12 like the optical channels 17 and 19, the light reflected by a mirror disposed close to the center of the mirror unit 20 may be blocked by a mirror near the circumference of the mirror unit 20. Also, if the mirrors 21 through 25 are formed of a semitransparent material, the beams of light exiting the plurality of optical channels 17 and 19 simultaneously enter the optical detector 18, and thus, the optical detector 18 cannot accurately measure the beams of light. FIG. 6 is a schematic top plan view illustrating the arrangement of the plurality of mirrors 21 through 25 in the optical detection apparatus 10 illustrated in FIG. 3. Such arrangement can overcome the above problems. Referring to FIG. 6, "X" designates the positions of the plurality of mirrors 21 through 25 in the mirror unit 20 and "O" designates the positions of the optical channels 17 and 19.

Referring to FIG. 6, the mirrors 21 through 25 of the mirror unit 20 are separated from each other by a predetermined azimuthal angle and disposed closer to the center of the mirror unit 20 in a predetermined azimuthal angle direction. That is, the plurality of mirrors 21 through 25 have the same radial positions as the optical channels 17a, 17b, 17c, 17d and 19, respectively, but are arranged at different azimuthal angles from one another on the mirror unit 20. Thus, when the mirror unit 20 rotates, the mirrors 21 through 25 may sequentially reflect the beams of light exiting the optical channels 17a, 17b, 17c, 17d and 19, respectively, to the optical detector 18.

The mirrors 21 through 24, which respectively correspond to the plurality of optical channels 17a through 17d, through which the light exiting the samples enter the filter wheel 12, are repeatedly installed in four regions of the mirror unit 20 which face the first through fourth color filters 12a through 12d, respectively. For example, referring to FIG. 6, a first set of mirrors 21a through 24a which respectively correspond to the optical channels 17a through 17d are installed in the region corresponding to the first color filter 12a, a second set of mirrors 21b through 24b which respectively correspond to the optical channels 17a through 17d are installed in the region corresponding to the second color filter 12b, a third set of mirrors 21c through 24c which respectively correspond to the optical channels 17a through 17d are installed in the region corresponding to the third color filter 12c, and a fourth set of mirrors 21d through 24d which respectively correspond to the optical channels 17a through 17d are installed in the region corresponding to the fourth color filter 12d. That is, in the mirror unit 20, the number of mirrors that correspond to each of the optical channels 17 is identical to the number of the first through fourth color filters 12a through 12d in the filter wheel 12. Meanwhile, there is only one of the mirror 25 which corresponds to the optical channel 19 which emits the mark light for indicating one cycle of the filter wheel 12.

The operation of the optical detection apparatus 10 is as follows. First, the filter wheel 12 and the mirror unit 20 are rotated in a counter-clockwise direction by a driving unit, for example, a spindle motor 15. The filter wheel 12 and the mirror unit 20 rotate at the same speed. Then, the light emitted from the samples enters the filter wheel 12 through the first through the fourth optical channels 17a through 17d and, simultaneously, the mark light for indicating one cycle of the filter wheel 12 enters the filter wheel 12 through the fifth optical channel 19. When the filter wheel 12 and the mirror unit 20 rotate, the mark light from the fifth optical channel 19 is reflected by the mirror 25 and enters the optical detector 18. The optical detector 18 receives the mark light and recognizes it as the start signal of a new channel. Then, the light from the fourth optical channel 17d, which is transmitted through the first color filter 12a, is reflected by the mirror 24a and enters the optical detector 18. Subsequently, the light from the third optical channel 17c, which is transmitted through the first color filter 12a, is reflected by the mirror 23a and enters the optical detector 18. Then, the beams of light from the second and the first optical channels 17b and 17a, which have been transmitted through the first color filter 12a, are sequentially reflected by the mirror 22a and the mirror 21a, respectively. Although the optical channel 19, which emits the mark light, is disposed closest to the center of the filter wheel 12 among the optical channels 17 and 19 in the present embodiment, the optical channels 17 and 19 may be disposed in different ways. Also, the filter wheel 12 and the mirror unit 20 may rotate in a clockwise direction.

When the filter wheel 12 and the mirror unit 20 rotate continuously in the counter-clockwise direction, the light from the fourth optical channel 17d, which is transmitted through the second color filter 12b, is reflected by the mirror 24b and enters the optical detector 18. Similarly, the beams of light from the third through the first optical channels 17c through 17a, which are transmitted through the second color filter 12b, are sequentially reflected by the mirrors 23b to 21b, respectively, and enter the optical detector 18. In this manner, the beams of light from the optical channels 17d through 17a, which are transmitted through the third color filter 12c, are sequentially reflected by the mirrors 24c through 21c, respectively, and enter the optical detector 18, and the beams of light from the optical channels 17d through 17a, which are transmitted through the fourth color filter 12d, are sequentially reflected by the mirrors 24d through 21d, respectively, and enter the optical detector 18.

After the filter wheel 12 and the mirror unit 20 rotate once, the mark light from the fifth optical channel 19 is reflected by the mirror 25 and enters the optical detector 18a second time. Thus, the optical detector 18 receives the mark light and recognizes it as the start signal of a new channel. At the same time, the beams of light emitted from other samples enter the optical detector 18 through the optical channels 17a through 17d. Then, the above process is repeated.

As explained above, the optical detection apparatus 10 may measure light from a plurality of multi-channel samples at high speed and various wavelengths using only one optical detector 18. In addition, the optical detection apparatus 10 has a simplified structure, and thus, can have a small size. The optical detection apparatus 10 illustrated in FIG. 3, for example, may be constructed with a radius of about 25 mm. Although only four optical channels 17a through 17d are used in the present embodiment, this example is given for the purpose of illustration and the number of the optical channels is not limited to four. When more optical channels are used, the number of mirrors in the mirror unit 20 must be increased accordingly.

Figure 7:
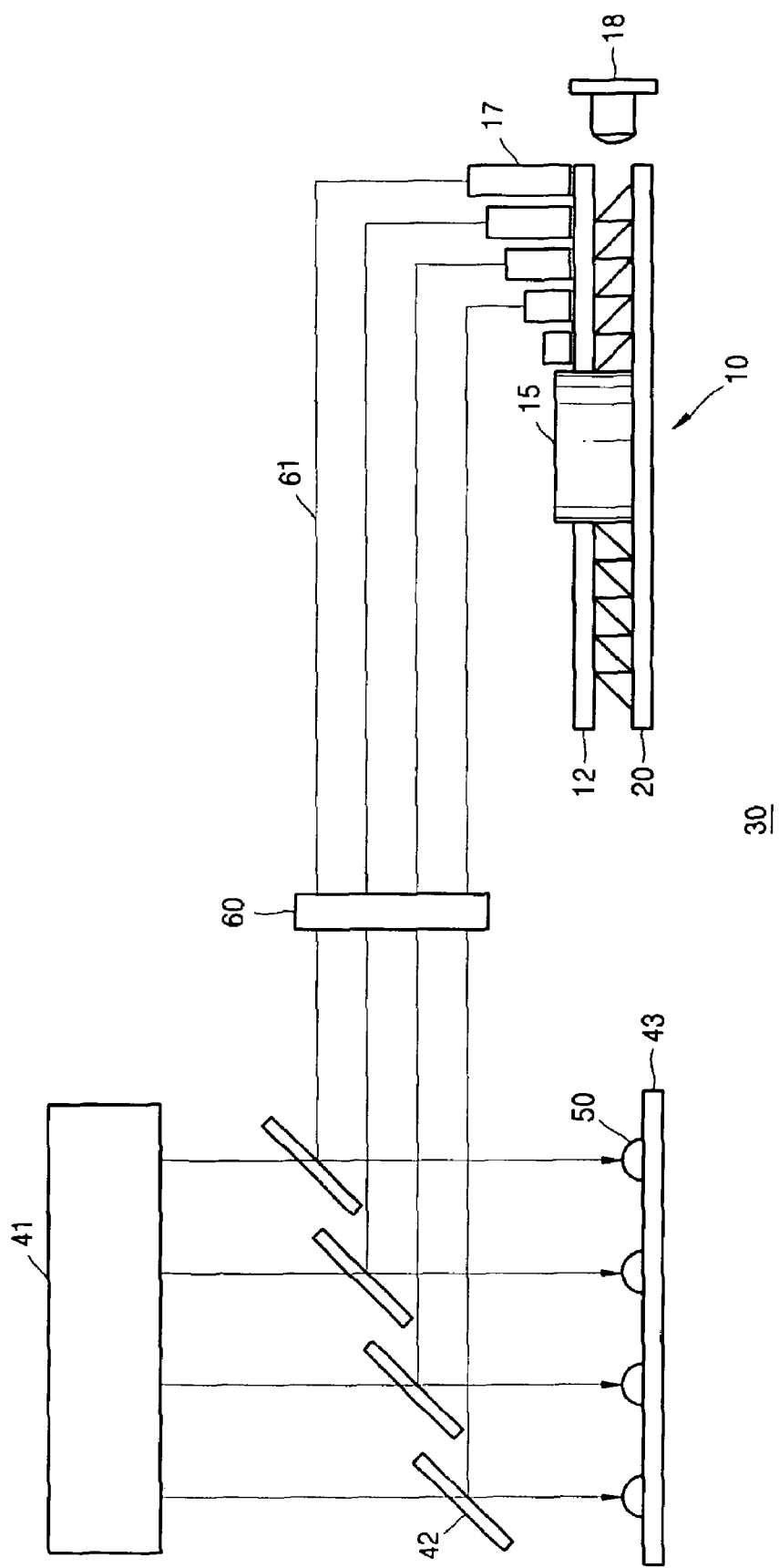
FIG. 7 is a schematic diagram of a multi-channel sample analyzer employing the optical detection apparatus illustrated in FIG. 3 according to an embodiment of the present invention.

FIG. 7 is a schematic diagram of a multi-channel sample analyzer employing the optical detection apparatus 10 according to an embodiment of the present invention. Referring to FIG. 7, the multi-channel sample analyzer 30 according to an embodiment of the present invention comprises a light source unit 41 for irradiating light onto a plurality of samples 50, an optical detection unit 10 for detecting light emitted from the plurality of samples 50, and an optical transport unit 60 and 61 for receiving the light emitted from the plurality of samples 50 and transporting the light to the optical detection unit 10. The multi-channel sample analyzer 30 may further comprise a sample holder 43 for holding the plurality of samples 50.

The light source unit 41 may have various structures, as described above regarding the conventional apparatus. For example, the light source unit 41 may have a plurality of light sources that separately irradiate light onto the plurality of samples 50. Alternatively, the light source unit 41 may irradiate a large area of light onto the plurality of samples 50 at once and the samples 50 can be scanned at a high speed while rotating the samples 50 or the light. The samples 50 are stained, for example, with various fluorescent dyes that emit light of different wavelengths. When the light is irradiated onto the samples 50, light beams having different wavelengths and intensities are emitted from the respective fluorescent materials. The emitted light beams are reflected by, for example, a dichroic mirror 42, and received by a light receiver 60. The light receiver 60 may be, for example, an optical fiber adaptor. The light beams received by the light receiver 60 are transported to the optical channels 17 through an optical fiber 61. Then, as described above, while rotating the filter wheel 12 and the mirror unit 20, the wavelengths and the intensities of the light beams emitted from the samples 50 are measured to analyze samples 50.

Although the multi-channel sample analyzer 30 is constructed such that the light beams emitted from the samples 50 are transported to the optical detection apparatus 10 via the light receiver 60 and the optical fiber 61 in FIG. 7, the multi-channel sample analyzer 30 may alternatively be constructed such that the light beams emitted from the samples 50 directly enter the optical channels 17. In this case, the optical channels 17 may be, for example, a refractive lens only for focusing the light.

A multi-channel fluorescence analyzer using the optical detection apparatus according to an embodiment of the present invention has been explained. However, the optical detection apparatus according to an embodiment of the present invention can be used as an optical detection unit for various types of multi-channel analyzers, as well as for the fluorescence analyzer.

As describe above, in an optical detection apparatus according to the present invention, a plurality of optical signals with various wavelengths can be sequentially detected at high speed using an optical detector and a filter wheel. Also, the optical detection apparatus has a simplified structure, and thus, can have a small size and have low production costs.

In addition, according to the present invention, the number of wavelengths which can be measured can be increased depending on the number of color filters in the wheel and the number of signals which can be detected can be controlled by varying the azimuthal angle between mirrors and the number of mirror sectors.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An optical detection apparatus for multi-channel multi-color measurement comprising:
   an optical detector;
   a filter wheel having at least two color filters connected to each other in the shape of a disk;
   a plurality of optical channels through which a plurality of beams of light enter the filter wheel; and
   a mirror unit including a plurality of mirrors for sequentially reflecting the plurality of beams of light transmitted through the filter wheel to the optical detector, wherein the mirror unit rotates together with the filter wheel.

2. The optical detection apparatus of claim 1, wherein the optical channels are arranged in a row above the filter wheel along the radius direction of the filter wheel on a line connecting the center of the filter wheel to the optical detector.

3. The optical detection apparatus of claim 2, wherein the optical channels farther from the optical detector are shorter than the optical channels closer to the optical detector.

4. The optical detection apparatus of claim 2, wherein some of the optical channels let the beams of light emitted from samples enter the filter wheel and one of the optical channels emits mark light for indicating one cycle of the filter wheel.

5. The optical detection apparatus of claim 1, wherein each of the mirrors of the mirror unit corresponds to one of the optical channels such that the beams of light exiting the optical channels are reflected to the optical detector and the mirrors are disposed at the same radial positions as the corresponding optical channels.

6. The optical detection apparatus of claim 5, wherein the mirrors in the mirror unit are disposed at different azimuthal angles from one another on the mirror unit such that the beams of light exiting the optical channels are sequentially reflected to the optical detector during the rotation of the mirror unit.

7. The optical detection apparatus of claim 6, wherein the mirrors are disposed closer to the center of the mirror unit in a predetermined azimuthal angle direction.

8. The optical detection apparatus of claim 6, wherein at least two of the mirrors correspond to each of the optical channels and the mirrors corresponding to each of the optical channels face the at least two color filters, respectively.

9. The optical detection apparatus of claim 8, wherein one of the optical channels emits mark light for indicating one cycle of the filter wheel and one of the mirrors corresponds to the optical channel emitting the mark light.

10. The optical detection apparatus of claim 1, further comprising a driving unit for rotating the filter wheel and the mirror unit.

11. A multi-channel sample analyzer comprising: a light source unit for irradiating light onto each of a plurality of samples; an optical detection unit for detecting light beams emitted from the plurality of samples; and an optical transport unit for receiving the light beams emitted from the plurality of samples and transporting them to the optical detection unit,
   wherein the optical detection unit comprises
   an optical detector;
   a filter wheel having at least two color filters connected to each other in the shape of a disk;
   a plurality of optical channels through which a plurality of beams of light transported from the optical transport unit enter the filter wheel; and
   a mirror unit including a plurality of mirrors for sequentially reflecting each of the plurality of beams of light transmitted through the filter wheel to the optical detector,
   wherein the mirror unit rotates together with the filter wheel.

12. The multi-channel sample analyzer of claim 11, wherein the optical transport unit comprises a light receiver for receiving the beams of light emitted from the samples and an optical fiber for transporting the beams of light from the light receiver to the optical detection unit.

13. The multi-channel sample analyzer of claim 11, further comprising a dichroic mirror for letting the light emitted from the light source unit proceed to the samples and letting the beams of light emitted from the samples proceed to the optical transport unit; a sample holder for holding the samples; and a driving unit for rotating the filter wheel and the mirror unit.

14. The multi-channel sample analyzer of claim 11, wherein the optical channels are arranged in a row above the filter wheel along the radius direction of the filter wheel on a line connecting the center of the filter wheel to the optical detector.

15. The multi-channel sample analyzer of claim 14, wherein the optical channels farther from the optical detector are shorter than the optical channels closer to the optical detector.

16. The multi-channel sample analyzer of claim 11, wherein each of the mirrors of the mirror unit corresponds to one of the optical channels such that the beams of light exiting the optical channels are reflected to the optical detector and the mirrors are disposed at the same radial positions as the corresponding optical channels.

17. The multi-channel sample analyzer of claim 16, wherein the mirrors in the mirror unit are disposed at different azimuthal angles from one another on the mirror unit such that the beams of light exiting the optical channels are sequentially reflected to the optical detector during the rotation of the mirror unit.

18. The multi-channel sample analyzer of claim 17, wherein at least two of the mirrors correspond to each of the optical channels and the mirrors corresponding to each of the optical channels face the at least two color filters, respectively.

19. The multi-channel sample analyzer of claim 18, wherein one of the optical channels emits mark light for indicating one cycle of the filter wheel and one of the mirrors corresponds to the optical channel emitting the mark light.

* * * * *